United States Patent [19]

Lary

[11] Patent Number: 5,697,944
[45] Date of Patent: Dec. 16, 1997

[54] UNIVERSAL DILATOR WITH EXPANDABLE INCISOR

[75] Inventor: Banning Gray Lary, Miami, Fla.

[73] Assignee: InterVentional Technologies Inc., San Diego, Calif.

[21] Appl. No.: 559,415

[22] Filed: Nov. 15, 1995

[51] Int. Cl.⁶ .................................................. A61B 17/32
[52] U.S. Cl. .......................... 606/159; 606/170; 606/180; 604/22
[58] Field of Search .......................... 606/1, 108, 159, 606/167, 170, 171, 180; 604/96; 128/898, 899

[56] References Cited

U.S. PATENT DOCUMENTS

| 3,635,223 | 1/1972 | Klieman. |
| 3,990,453 | 11/1976 | Douvas et al.. |
| 4,273,128 | 6/1981 | Lary. |
| 4,465,072 | 8/1984 | Taheri. |
| 4,685,458 | 8/1987 | Leckrone .............................. 606/159 |
| 4,696,667 | 9/1987 | Masch. |
| 4,723,549 | 2/1988 | Wholey et al.. |
| 5,009,659 | 4/1991 | Hamlin et al.. |
| 5,100,425 | 3/1992 | Fischell et al.. |
| 5,156,610 | 10/1992 | Reger. |
| 5,196,024 | 3/1993 | Barath. |
| 5,320,634 | 6/1994 | Vigil et al.. |

FOREIGN PATENT DOCUMENTS 938977 6/1982 U.S.S.R..

*Primary Examiner*—William Lewis
*Attorney, Agent, or Firm*—Nydegger & Associates

[57] ABSTRACT

A device for incising and dilating a stenosis in a vessel of a patient includes a dilator housing and a plurality of blades which can be selectively extended from the housing. Specifically, the housing is formed to surround a chamber and the chamber contains an inflatable balloon. The plurality of blades are mounted on the inflatable balloon and pass through slits in the housing. The housing is attached to a placement catheter which includes a lumen for inflating and deflating the balloon. In the operation of the device, the balloon is selectively inflated within the chamber to move the device between a retracted and an expanded configuration. In the retracted configuration, the balloon is deflated and the blades are withdrawn into the housing and the housing is used as a dilator. In the expanded configuration, the balloon is inflated and the blades are extended through the slits in the housing and the device is used as an incisor.

15 Claims, 2 Drawing Sheets

UNIVERSAL DILATOR WITH EXPANDABLE INCISOR

FIELD OF INVENTION

The present invention pertains generally to cardiovascular surgical tools. More particularly, the present invention pertains to surgical tools which are useful for clearing a stenosis from a vessel of a patient. The present invention is particularly, but not exclusively, useful as a mechanical dilator which can be selectively altered in its configuration to create incisions in a stenosis as the dilator is being distally advanced through the stenosis.

BACKGROUND OF THE INVENTION

Stenotic segments in the vessels and arteries of a patient can develop for many different reasons and can have different adverse effects on the patient. Depending on the location of the particular stenosis, the patient can experience cardiac arrest, stroke, or tissue and organ necrosis. Further, the severity of damage to the patient will, at least to some extent, depend on the nature of the stenosis and the extent of its development. Suffice it to say, stenotic segments can develop throughout a patient's cardio-vascular system, and can vary in size, shape and composition. Consequently, they vary in the degree to which they occlude blood flow through the vessel.

A stenosis in a vessel can be quite extensive and occlude a substantial length of a vessel. On the other hand, some stenoses are quite short. Further, some stenoses are highly calcified while other are not. The consequence is that, depending on the nature of the particular stenosis, some surgical tools and procedures are more appropriate than are others for clearing the stenosis.

Angioplasty is one of several types of medical procedures which has been widely used in recent years to surgically clear a stenosis in a vessel. More specifically, in an angioplasty procedure, a balloon is placed across the stenosis where it is inflated to dilate the stenosis.

Atherectomy is another type of medical procedure which, as an alternative to angioplasty, has been an acceptable and widely used procedure for surgically clearing a stenosis from a vessel. Quite unlike an angioplasty procedure, however, an atherectomy procedure results in the clearing of the vessel by cutting and removing the stenotic plaque from the vessel.

Still another type medical procedure, though somewhat like angioplasty in its effect on the stenosis, is a dilatation probe. For a procedure using a dilatation probe, the stenosis is simply approached by the probe and the probe is then pushed or urged through the stenosis. In an aggressive procedure, the probe can be moved back and forth through the stenosis. In any event, due to the dilating or spreading effect of the probe, the stenosis can be cleared. Further, in comparison with either an angioplasty or an atherectomy procedure, the use of a dilatation probe is relatively simple.

It has been determined that the dilatation of a stenosis is greatly facilitated if the stenosis is incised before the dilatation. Consequently, several devices have been proposed for this purpose. For example, U.S. Pat. No. 4,273,128 which issued to Lary for and invention entitled "Coronary Cutting and Dilating Instrument" discloses a serial combination of a distal longitudinal incisor and a proximal dilatation balloon. Further, U.S. Pat. No. 5,320,634 which issued to Vigil et al. for an invention entitled "Balloon Catheter with Seated Cutting Edges" discloses a device in which the incising blades are carried on the surface of the angioplasty balloon. Both of these patents are assigned to the same assignee as the present invention.

There is, of course, an ever present danger when sharp instruments are inserted into and through a vessel of a patient to incise tissue. Very importantly, the incising instrument, i.e. a sharpened blade, needs to be effectively covered during its insertion into the vessel in order to protect the vessel from inadvertent incisions. Such protection becomes increasingly more important as the distance for travel of the incising instrument through the vessel increases.

The present invention recognizes that an incisor/dilator surgical tool may be well suited for certain procedures. Several factors, however, need to be considered when determining the most desirable structure for an expandable incisor/dilator surgical tool and its method of use. First, it happens that angioplasty and atherectomy procedures may be performed in the coronary arteries, the carotid arteries, the renal arteries, and in the peripheral arteries. Each set of arteries is different and presents different challenges to the angioplasty or atherectomy procedure. Further, there is the need to satisfy the personal preferences of the particular surgeon who is to perform the atherectomy operation. Clearly, different surgeons can have different approaches to the solution of the same problem. With all of this in mind, there is the need to provide a structure which is best suited and configured for performance of the particular task. The present invention provides such a structure for consideration and use by the operating physician.

In light of the above, it is an object of the present invention to provide a surgical dilator tool with expandable incisors which can selectively extend blades from the tool for incision of a stenotic segment. Another object of the present invention is to provide a surgical dilator tool with expandable incisors which keeps its incising blades covered, to protect against inadvertent incision of the vessel wall, during transit of the tool through an artery or vessel to the stenosis. Yet another object of the present invention is to provide a surgical tool which can act simply as a dilator or, alternatively, as an incisor. Still another object of the present invention is to provide a surgical dilator tool with expandable incisors which is relatively easy to manufacture, is simple to operate and is comparatively cost effective.

SUMMARY OF THE INVENTION

In accordance with the present invention, a device for incising and dilating a stenosis in a vessel of a patient includes an ellipsoidal dilator housing formed to surround a chamber. The ellipsoidal shape of the dilator housing defines a longitudinal axis and is chosen for its ability to dilate a stenosis as the dilator housing is either advanced or withdrawn through the stenosis in a vessel of the patient. It may be appreciated, however, that shapes other than the ellipsoidal shape, may be used for the dilator housing and are equally practical.

A placement catheter is joined to the proximal end of the dilation housing. The connection between the placement catheter and the dilation housing positions the placement catheter to extend away from the dilation housing in a proximal direction in a substantially coaxial fashion with the longitudinal axis defined by the dilation housing. The placement catheter is formed around a lumen and the lumen is connected in fluid communication with the chamber of the dilation housing. Preferably, the placement catheter is formed from a semi-rigid, resilient material which allows the placement catheter to be used to push and pull the dilation housing within the vessel of the patient.

An inflatable balloon is positioned inside of the chamber of the dilation housing. The inflatable balloon is connected to the lumen of the placement catheter allowing the placement catheter to be used as a fluid conduit to inflate and deflate the inflatable balloon. Alternatively, the inflatable balloon may be connected to a separate inflation catheter which passes through the placement catheter.

A plurality of blades are mounted to the surface of the inflatable balloon and a series of slits are included in the dilation housing to allow for the passage of the blades through the dilation housing. The blades are preferably constructed from a metal material and are dimensioned to extend along the length of the dilator housing in line with its longitudinal axis. Each blade is spaced radially around the balloon.

The combination of the inflatable balloon and the blades allows the device of the present invention to move between two configurations. In the first, or retracted configuration, the blades mounted to the balloon are contained entirely within the dilation housing. In this retracted configuration, the dilation housing may be forced to pass through and mechanically dilate the stenosis. In the second, or extended configuration, the inflated balloon causes the blades to protrude radially through the slits in the dilation housing. When so extended, the blades are used to incise the stenosis during a distal advancement of the dilator housing.

In the operation of the device of the present invention, fluid is passed through the placement catheter to selectively inflate the balloon and move the blades between the retracted and extended configurations. In the retracted configuration, the blades are withdrawn into the chamber and held there to configure the device as a dilator. With the device configured as a dilator, no blades extend from the housing and the ellipsoidal shaped housing can be moved distally and proximally through a stenosis in a vessel to dilate the stenosis. On the other hand, when the balloon is inflated, the blades extend from the housing through the slits. This configures the device as an incisor. With the incisor configuration, a distal advancement of the device will cause the blades to make initial incisions into the stenosis to facilitate subsequent dilatation of the stenosis. As is to be appreciated, the housing will act as a dilator when the blades are extended therefrom (expanded configuration), as well as when the blades are withdrawn into the housing (retracted configuration).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
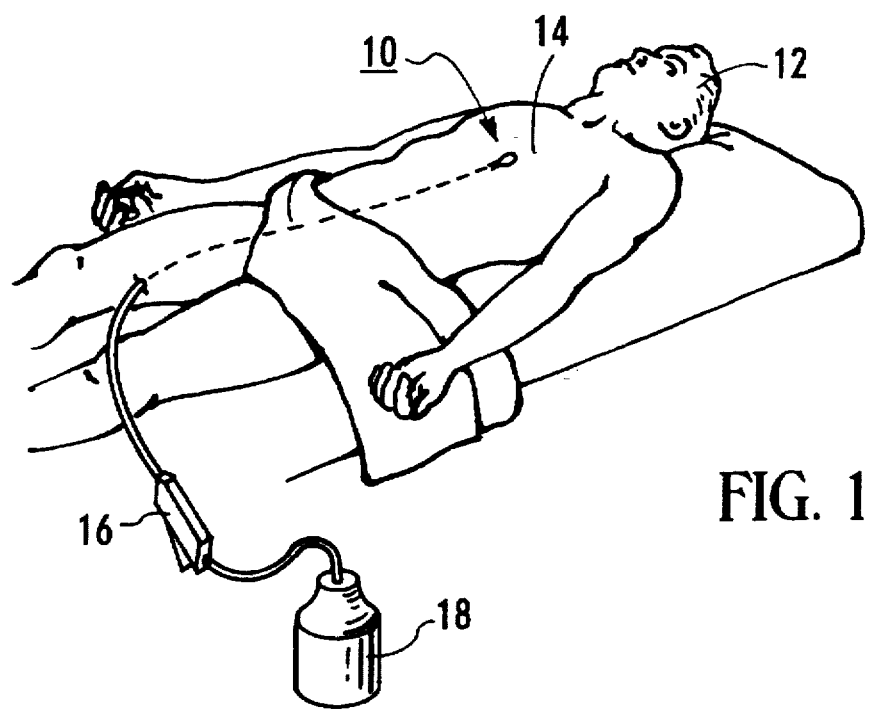
FIG. 1 is a view of a patient and the intended environment for operation of the surgical dilator tool with expandable incisors of the present invention.

Referring initially to FIG. 1, the surgical device 10 of the present invention is shown inserted into the vessel of a patient 12. For purposes of illustration, the device 10 is shown in an operational position after being advanced through the femoral artery and toward the heart 14 of the patient 12. It is to be appreciated, however, that the device 10 is useful in vessels throughout the cardiovascular system of patient 12 and may be introduced into the vessel wherever it is most convenient to do so. FIG. 1 also shows that the device 10 is connected to a control unit 16 which selectively controls the application of a fluid pressure source 18.

Figure 2:
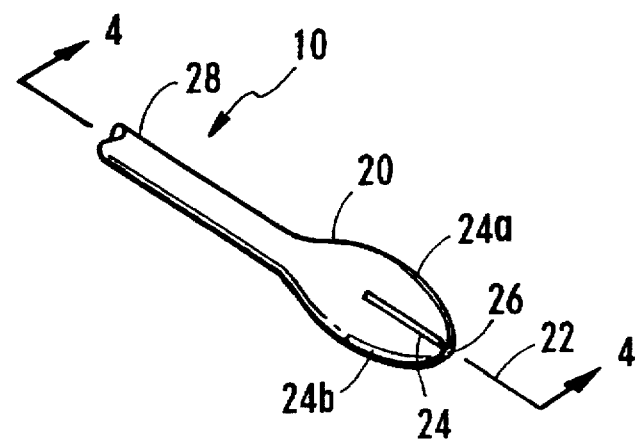
FIG. 2 is an isometric view of the surgical dilator tool with expandable incisors of the present invention shown in the retracted configuration.

Referring now to FIG. 2, it will be seen that the device 10 of the present invention includes a housing 20 which is generally ellipsoidal in shape and defines a longitudinal axis 22. Housing 20 is formed with a plurality of slits 24 of which slits 24a and 24b are exemplary. Each slit 24a, 24b is oriented to substantially parallel the longitudinal axis 22. At the distal end of housing 20, an opening 26 is formed. Preferably, housing 20 is made of a hard, rigid, plastic such as ABS.

Continuing with reference to FIG. 2, it may be seen that the proximal end of the housing 20 is connected to a placement catheter 28. The placement catheter 28 provides a means whereby the housing may be positioned within the vessel of a patient, such as patient 12. Therefore, the placement catheter 28 is preferably fabricated from a material which combines sufficient rigidity and strength to transmit the pushing and pulling forces used to position the housing 20.

For the purposes of the present invention, the configuration of the device 10 shown in FIG. 2 may be referred to as the retracted configuration. Furthermore, it is easily appreciated that the combination of the ellipsoidal housing 20 and the placement catheter 28, allows the device 10 to be used as a dilator whenever the device 10 is mechanically advanced through an occluding stenosis.

Figure 3:
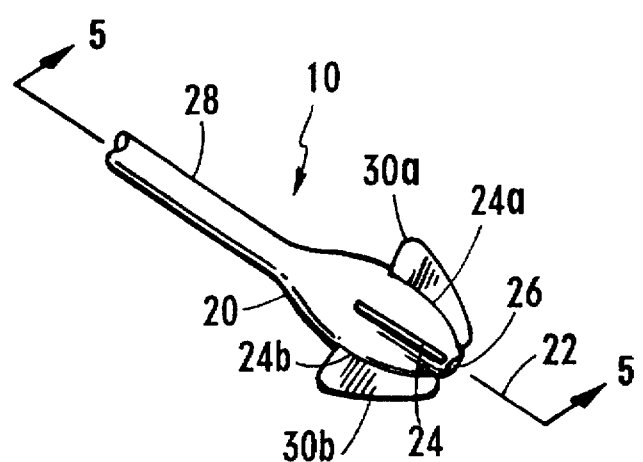
FIG. 3 is an isometric view of the surgical dilator tool with expandable incisors of the present invention shown in the expanded configuration.

Turning now to FIG. 3, the device 10 of the present invention is shown and includes all of the structural details described in reference to FIG. 2. In FIG. 3, however, it may be seen that a plurality of blades 30a, 30b extend radially away from the housing 20. In greater detail, it may be seen that each of the blade 30a, 30b extends from a respective slit 24a, 24b. The extended blades 30a and 30b indicate that the device 10, as shown in FIG. 3, is in the extended configuration wherein the device 10 may be used as an incisor.

Figure 4:
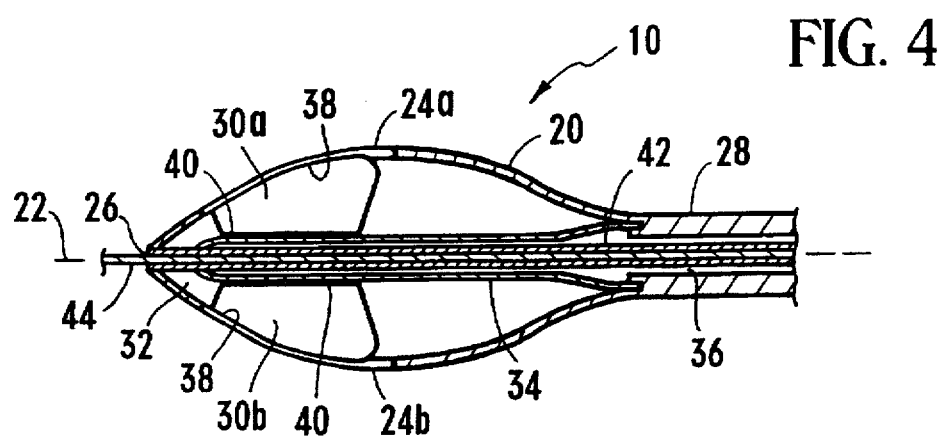
FIG. 4 is cross-sectional view of the surgical dilator tool with expandable incisors of the present invention taken along the line marked 4—4 in FIG. 2.
Figure 5:
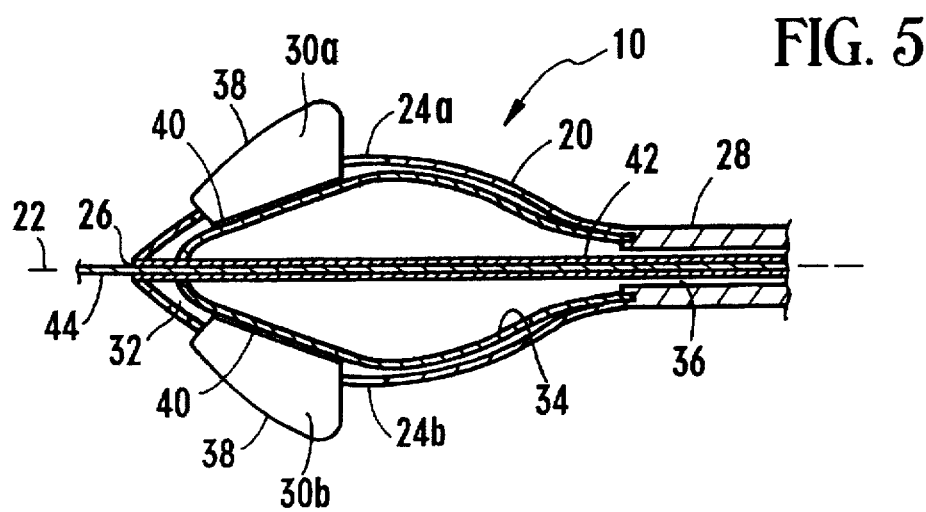
FIG. 5 is cross-sectional view of the surgical dilator tool with expandable incisors of the present invention taken along the line marked 5—5 in FIG. 3.

The structural details that allow the device 10 to move between the retracted configuration, shown in FIG. 2, and the extended configuration shown in FIG. 3, may be better appreciated by reference to FIGS. 4 and 5. Referring initially to FIG. 4, it may be seen that the housing 20 is formed to surround a chamber 32 which contains an inflatable balloon 34. Additionally, it may be seen that the placement catheter 28 is formed to include an inflation lumen 36 which connects the inflatable balloon 34 in fluid communication with the fluid pressure source 18. The connection between the inflatable balloon 34, the inflation lumen 36 allows fluid to be passed through the inflation lumen 36 from the fluid pressure source 18 to selectively inflate the balloon 34. Withdrawal of fluid through the inflation lumen 36 causes the balloon 34 to deflate. Alternatively, the inflatable balloon 34 may be connected to a separate inflation catheter (inflation catheter not shown) and the inflation catheter may be passed through a lumen within the placement catheter 28.

As shown, each blade 30a, 30b is positioned within the chamber 32 and attached to the balloon 34. In more detail, each blade 30a, 30b is formed to include a cutting edge 38 and a basal strip 40. The basal strip 40 included in each blade 30a, 30b gives the blade 30a, 30b an inverted T-shape (not shown). The basal strip 40 of each blade 30a, 30b is attached to the balloon 34 with a suitable adhesive, allowing the blade 30a, 30b to move with the balloon 34 as the balloon 34 inflates or deflates.

Inflation of the balloon 34, as shown in FIG. 5, causes each blade 30a, 30b to project radially from a respective slit 24a, 24b. In this fashion, the balloon 34 may be inflated or deflated to cause the device 10 to move between the retracted configuration (shown in FIGS. 2 and 4) where the blades 30a, 30b are positioned within the chamber 32, and the extended configuration (shown in FIGS. 3 and 5), wherein each blade 30a, 30b projects from the housing 20, or any intermediate configuration. Preferably, each of the blades 30a, 30b is dimensioned to ensure that the cutting edge 38 projects into the slits 24a, 24b when the device 10 adopts the retracted configuration. In this manner, the slits 24a, 24b provide a guide, for directing the blades 30a, 30b as the balloon 34 inflates to move the device 10 from the retracted configuration to the expanded configuration.

In some cases, it may be desirable to use the present invention in cooperation with a guidewire. To accomplish this result, as shown in FIGS. 4 and 5, the placement catheter 28 may be formed with a guidewire lumen 42 which extends through the inflatable balloon 34 and housing 20. A guidewire 44 may be inserted through the opening 26 of the housing 20 and passed through the guidewire lumen 42 of the placement catheter 28.

OPERATION

Figure 6:
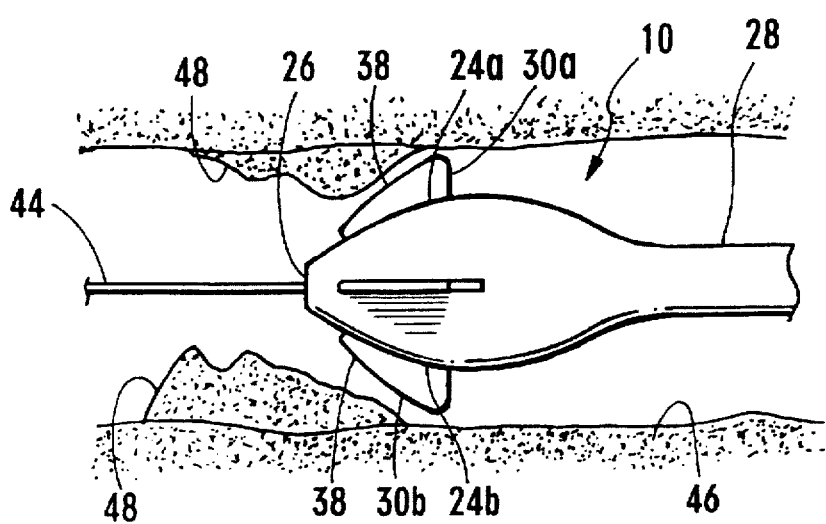
FIG. 6 is a plan view of the present invention operationally positioned within an arterial vessel of a patient.

As best appreciated by reference to FIG. 6, operation of the device 10 of the present invention begins by prepositioning the guidewire 44 in the vessel 46 of patient 12. In this fashion, guidewire 44 establishes a pathway to the stenotic segment 48 which is to be dilated. The device 10 is then inserted over the guidewire 44 by passing the guidewire 44 through the opening 26 of the housing 20 and through the guidewire lumen 42 of the placement catheter 28. The device 10 is then advanced over the guidewire 44 to position the housing 20 at the site of the stenotic segment 48. During the advancement of device 10 over guidewire 44, the device 10 is preferably configured in the retracted configuration (shown in FIGS. 2 and 4). In this configuration the balloon 34 is deflated and the blades 30a, 30b are withdrawn into the chamber 32. In this manner, inadvertent contact between the blades 30a, 30b and the vessel 46 is prevented.

Once the housing 20 of device 10 is positioned at the site of the stenotic segment 48, the control unit 16 may be used to activate the fluid supply 18 to pass fluid under pressure through the inflation lumen 36 to inflate the balloon 34. The inflation of the balloon 34 causes the device 10 to adopt the extended configuration with the blades 30a, 30b extended radially from the housing 20 through slits 24a, 24b. Consequently, any further movement of device 10 along guidewire 44 in the distal direction will cause blades 30a, 30b to incise the stenosis 48. This incising will then be immediately followed with a dilatation of the stenosis caused by the simultaneous distal advancement of housing 20.

It is to be appreciated that, at the stenosis 48, device 10 can be manipulated back and forth in the distal and proximal directions through the vessel 46 of patient 12 as desired by the user. Thus, incision and dilatation of the stenotic segment 48 can be as aggressive as is required. Further, as deemed necessary, the control unit 16 may be manipulated to pass fluid into balloon 34 to selectively extend blades 30a, 30b. Thus, the extension of blades 30a, 30b from housing 20 can be varied to configure device 10 as an incisor/dilator having different incising capabilities. In any case, control unit 16 may be manipulated to withdraw fluid from balloon 34, retracting blades 30a, 30b and configuring device 10 as a dilatator only.

While the particular surgical dilator tool with expandable incisors herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A device for incising and dilating a stenosis in a vessel which comprises:

an inflatable balloon;

a plurality of blades mounted onto said balloon;

a housing made of a rigid plastic and formed with a plurality of slits and surrounding a chamber therein, said balloon being positioned in said chamber with each said blade aligned with a respective said slit;

a placement catheter, said placement catheter being formed with a lumen and having a distal end, said distal end of said placement catheter being attached to said housing for positioning of said housing in said vessel; and a fluid pressure source attached in fluid communication with said balloon for inflation of said balloon in said chamber between a first position wherein said blades are withdrawn into said housing for use of said device as a dilator and a second position wherein said blades extend through said slits of said housing for use of said device as an incisor.

2. A device as recited in claim 1 wherein said housing is substantially ellipsoidal in shape.

3. A device as recited in claim 1 wherein said device further comprises a guidewire insertable through said lumen, said guidewire being prepositionable in a vessel of a patient for advancing said device to a stenosis in the vessel.

4. A device as recited in claim 1 wherein said blades are made of a metal.

5. A device as recited in claim 1 wherein said placement catheter is made of PET.

6. A device for incising and dilating a stenosis in a vessel which comprises:

an inflatable balloon;

a plurality of blades mounted on said balloon;

a housing made of a rigid plastic for dilating said stenosis in said vessel, said housing shaped to surround said balloon;

means attached to said housing for positioning said housing within said vessel; and means attached to said balloon for inflation of said balloon between a first position wherein said blades are withdrawn into said dilating means for use of said device as a dilator and a second position wherein said blades extend from said dilating means for use of said device as an incisor.

7. A device as recited in claim 6 wherein said blades are made of a metal.

8. A device as recited in claim 6 wherein said housing is formed with a plurality of slits to surround a chamber therein, said balloon being positioned in said chamber with said blades aligned with said slits.

9. A device as recited in claim 6 wherein said housing is substantially ellipsoidal in shape.

10. A device as recited in claim 6 wherein said positioning means comprises a placement catheter, said placement catheter being formed with a lumen and having a distal end, said distal end of said placement catheter being attached to said housing for positioning of said housing in said vessel.

11. A device as recited in claim 10 wherein said placement catheter is made of PET.

12. A device as recited in claim 10 wherein said device further comprises a guidewire insertable through said lumen, said guidewire being prepositionable in a vessel of a patient for advancing said device to a stenosis in the vessel.

13. A method for incising and dilating a stenosis in a vessel of a patient which comprises the steps of:

advancing a device to the stenosis through the vessel, said device comprising an inflatable balloon, a plurality of blades mounted to said balloon, a housing formed with a plurality of slits to surround a chamber therein, said balloon being positioned in said chamber with said blades aligned with said slits, a catheter attached to said housing for positioning of said housing in said vessel, said catheter attached in fluid communication with said balloon for inflation of said balloon in said chamber between a first position wherein said blades are withdrawn into said housing and a second position wherein said blades extend through said slits of said housing;

selectively inflating said balloon to extend said blades through said slits of said housing to incise said stenosis;

selectively deflating said balloon to withdraw said blades into said housing; and moving said housing of said device in the vessel and through the stenosis to dilate the stenosis.

14. A method as recited in claim 13 wherein said balloon and said catheter are formed with a contiguous lumen and wherein said advancing step is accomplished by the steps of:

prepositioning a guidewire in the vessel and through the stenosis; and inserting said guidewire into said lumen; and advancing said device over said guidewire and into contact with the stenosis.

15. A method as recited in claim 13 further comprising the steps of:

prepositioning a guide catheter in the vessel, said guide catheter being formed with a lumen for receiving said housing and said catheter therethrough to guide said housing to the stenosis; and advancing said housing and said catheter through said lumen of said guide catheter and into contact with the stenosis.

* * * * *